(12) United States Patent
Chainer et al.

(10) Patent No.: US 6,501,390 B1
(45) Date of Patent: Dec. 31, 2002

(54) METHOD AND APPARATUS FOR SECURELY DETERMINING ASPECTS OF THE HISTORY OF A GOOD

(75) Inventors: Timothy J. Chainer, Mahopac, NY (US); Claude A. Greengard, Chappaqua, NY (US); William R. Pulleyblank, Croton-on-Hudson, NY (US); Charles P. Tresser, Mamaroneck, NY (US); Chai W. Wu, Poughquag, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/228,231

(22) Filed: Jan. 11, 1999

(51) Int. Cl.⁷ .............................................. G08B 21/00
(52) U.S. Cl. .................. 340/870.16; 340/571; 340/522; 235/440; 206/459.1
(58) Field of Search ............................... 340/572.7, 571, 340/539, 10.41, 573.4, 10.5, 870.11, 870.16, 521, 522; 235/440, 472.02, 419; 382/313, 305; 374/102; 206/459.1

(56) References Cited

U.S. PATENT DOCUMENTS

| | | | |
|---|---|---|---|
| 4,063,229 A | | 12/1977 | Welsh et al. ................. 340/571 |
| 4,092,524 A | * | 5/1978 | Moreno ....................... 235/419 |
| 4,102,493 A | * | 7/1978 | Moreno ....................... 235/419 |
| 4,242,663 A | | 12/1980 | Slobodin ..................... 235/380 |
| 4,593,384 A | * | 6/1986 | Kleijne | 
| 4,646,090 A | | 2/1987 | Mawhinney .................. 342/44 |
| 4,746,830 A | * | 5/1988 | Holland ....................... 310/313 |
| 4,787,246 A | * | 11/1988 | Komatsu et al. ............... 73/492 |
| 4,789,804 A | * | 12/1988 | Karube et al. ............... 310/311 |
| 4,813,541 A | * | 3/1989 | Velasco et al. .......... 206/459.1 |
| 4,827,395 A | * | 5/1989 | Anders ................... 340/825.72 |
| 4,864,110 A | | 9/1989 | Guillou ....................... 235/380 |
| 4,952,928 A | * | 8/1990 | Carroll ..................... 340/10.41 |
| 4,972,099 A | | 11/1990 | Amano et al. ............... 382/313 |
| 4,995,085 A | | 2/1991 | Kern et al. .................. 381/320 |
| 5,010,560 A | | 4/1991 | Janney et al. ................. 377/20 |
| 5,028,918 A | * | 7/1991 | Giles ....................... 340/10.41 |
| 5,051,725 A | * | 9/1991 | Caccitolo .................... 220/810 |
| 5,140,634 A | | 8/1992 | Guillou et al. ............... 713/180 |
| 5,159,629 A | | 10/1992 | Double et al. ............... 713/192 |
| 5,332,315 A | * | 7/1994 | Baker ......................... 374/102 |
| 5,682,143 A | | 10/1997 | Brady et al. ............. 340/572.7 |
| 5,995,898 A | * | 11/1999 | Tuttle ......................... 701/102 |
| 6,112,152 A | * | 8/2000 | Tuttle ......................... 701/115 |
| 6,167,333 A | * | 12/2000 | Gehlot ......................... 701/35 |
| 6,287,671 B1 | * | 9/2001 | Bright et al. .................. 156/84 |

FOREIGN PATENT DOCUMENTS

| | | |
|---|---|---|
| DE | 197 05 615 A1 | 6/1998 |
| DE | 297 17 395 U1 | 12/1998 |
| GB | 2 308 947 | 7/1997 |

* cited by examiner

*Primary Examiner*—Michael Horabik
*Assistant Examiner*—Albert K. Wong
(74) *Attorney, Agent, or Firm*—Whitham, Curtis & Christofferson, P.C.; Stephen C. Kaufman

(57) ABSTRACT

The present invention provides methods and apparatus to detect and reliably record the physical history of a product including effects due to one or more of the following: 1) product use 2) handling 3) tampering and 4) environment of the product (as changes in the environment, such as excessive temperatures, humidity, or shocks, can result in degradation to a product). The apparatus includes a "smart card", or, more generally, "smart token", in combination with one or more sensors which record the external influences on the product and/or the environment and records those changes in an encrypted form. This information can then be verified by any individual who is equipped with a (possibly public) decryption key, but capability to modify this information, depending on the application, is restricted to those with access to the encrypting key. Furthermore, the apparatus contains authentication information which can be reliably verified, in particular to confirm that the apparatus is attached to the product it supposed to be attached to.

23 Claims, 2 Drawing Sheets

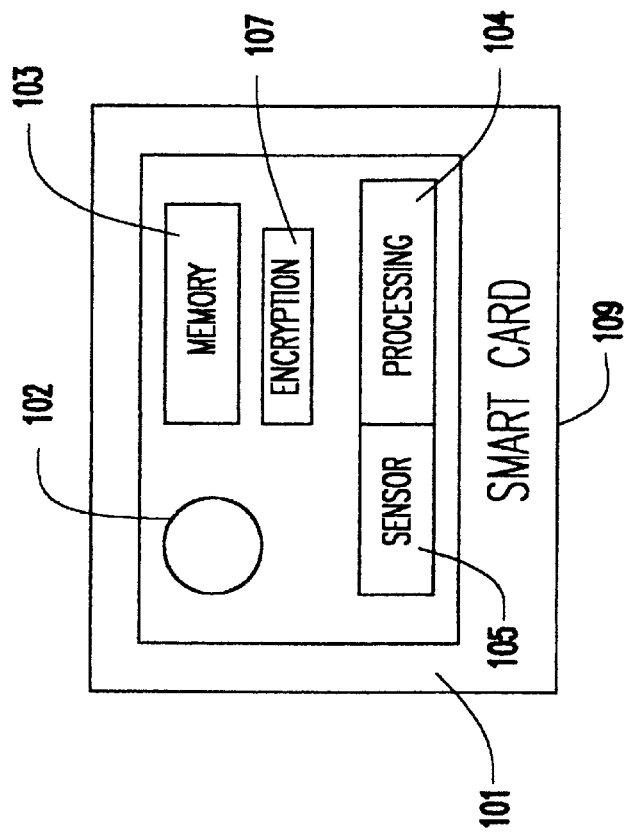
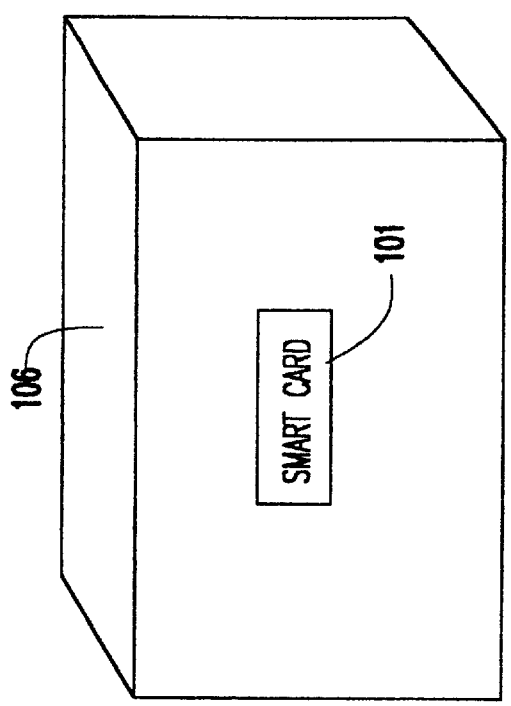
FIG.1B
FIG.1A

METHOD AND APPARATUS FOR SECURELY DETERMINING ASPECTS OF THE HISTORY OF A GOOD

BACKGROUND OF THE INVENTION

1. Field of the Invention

The present invention generally relates to security of consumer goods and, more particularly, to the use of smart tags in maintaining product security.

2. Background Description

There is a need for certain products to be equipped with some apparatus which can provide information about the current state of the product as a result of events the product was subjected to prior to becoming in the possession of a potential consumer. Examples include the state of medical or food products prior to their being used by a consumer.

Also, consumers sometimes have the right and/or the need to know whether a product is brand new or not. This is especially true of expensive items. There is also a need for a product to be equipped by some apparatus which can record some aspects of the product history, for example in the case of automobiles where today odometers indicate, not very securely, one aspect of the history of the automobile.

Another context for the invention is the fact that, in some cases, the containers of some products are reused by the manufacturer, and the consumer would like to know if the product in the container is new or not, and if the container has been reused by a third, unauthorized, party. There is also a need for a method to detect whether the product has deteriorated, either because of defects, or because its expiration date has passed, or because of unwanted change in the environment, for instance in the form of excessive cold, heat or humidity. These scenarios require an apparatus which can detect the physical forces a product was subjected to as a result of use, handling, tampering or environmental factors. For either human intervention or environmental factors, it may be important in some circumstances that the recorded history of such events be very difficult to modify or counterfeit.

The prior art contains many methods involving seals and enclosures which allow one to detect when a package has been tampered with. Such prior art go way back in history, and a multitude of improvements, with very general or very specific uses, have been proposed which benefit from the general progress of technology. For example, U.S. Pat. No. 5,159,629 to Glen P. Double and Steve H. Weingart describes an intrusion barrier for protecting an electronic assembly from tampering. The prior art also contains methods of recording chronological information such as a data logger which stores information on a product as described in U.S. Pat. No. 5,010,560 to Mark A. Janney, Roger Newey, and Irwin J. Robinson.

However, these methods do not overcome the problem of providing a tamper evident history of a product and/or of its environment. The prior art does not allow the information about the history of a product and/or of its environment to be securely recorded and kept.

SUMMARY OF THE INVENTION

It is therefore an object of the present invention to provide a novel improvement on the prior art of tamper evident packaging which can detect when a product has been tampered with and resists the efforts of a tamperer, or anyone else who would benefit from hiding the tampering, or to hide the signs of tampering.

In the following, terms such as "impossible to change" or "tamper-proof" should be understood to describe situations in which sufficient resistance to tampering is provided to make successful attacks rare due to cost/benefit issues, since codes, etc., can theoretically be broken if sufficient resources are brought to bear on the attack.

The invention uses a smart card, as described in U.S. Pat. Nos. 3,971,916, 4,007,355, 4,092,524, and 4,102,493 to Roland Moreno, or, more generally, a smart token, in combination with sensors attached to the product and/or to the smart card: upon tampering, or as a response to other circumstances, the sensors generate signals which are encrypted and recorded in the memory or storage device of the smart card attached to the product.

Recall that, for example, by using a zero-knowledge protocol, a smart card can be authenticated but cannot be duplicated. This technology has been disclosed for instance in U.S. Pat. No. 5,140,634 to Guillou, et al. This is the property which characterizes a smart card. Accordingly, in the rest of the present disclosure, any electronic component with these properties and which has some memories and/or some processing capabilities, will be called "a smart token" or "a smart card", even if it does not actually take any form resembling a card. A general reference to smart card technology and applications can be found in *Smart Cards: A Guide to Building and Managing Smart Card Applications*, by Henry Dreifus and J. Thomas Monk, John Wiley & Sons, 1998.

When the product or its packaging is tampered with, some attribute of the product or its environment changes. This change is what is detected by (at least some of) the sensors attached to a smart card, and the smart card will record this change irreversibly by erasing or writing some information within the smart card memory. The smart card also can be made duplication resistant by using a zero-knowledge protocol so that only the manufacturer of the original product, and/or possibly a trusted third party, for example, can produce or buy such smart cards. The smart card also can record the history of these changes in its internal memory.

BRIEF DESCRIPTION OF THE DRAWINGS

The foregoing and other objects, aspects and advantages will be better understood from the following detailed description of a preferred embodiment of the invention with reference to the drawings, in which:

FIG. 1A is an isometric diagram showing a smart tag attached to a product;

FIG. 1B is a plan view showing detail of the smart tag shown in FIG. 1; and

DETAILED DESCRIPTION OF A PREFERRED EMBODIMENT OF THE INVENTION

Figure 2:
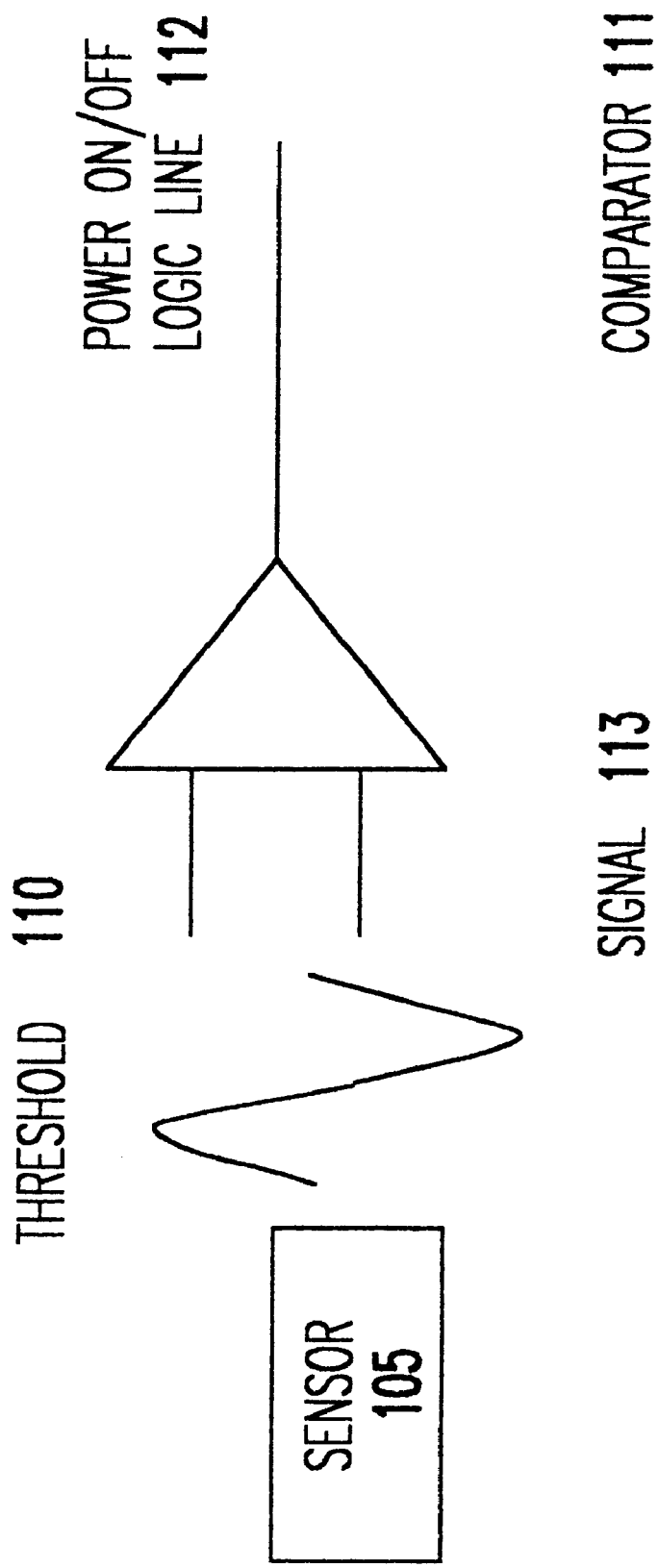
FIG. 2 is a schematic diagram showing the path from sensors to production of an electrical signal.

Referring now to the drawings, and more particularly to FIG. 1A, there is shown a smart card 101 attached to a product 106. As shown in FIG. 1B, the smart card is powered by a small power source such as a battery 102. In addition to the normal components in a smart card, such as memory or storage device 103 and processing unit 104, and encryption module 107, the smart card is also connected to a sensor 105 (or some number of sensors) which can detect changes in the product and/or the environment due to tampering.

The encryption module can use any of the well-known (public or private) encryption algorithms such as Rivest, Shamir and Adleman (RSA) or Data Encryption Standard (DES), as described for example in *Handbook of Applied Cryptography*, by Alfred J. Menezes, Paul C. van Oorschot and Scott A. Vanstone, CRC Press, 1997. A discussion on cryptographic issues related to smart cards can be found in the aforementioned book by Dreifus and Monk. The encryption algorithms can be implemented as software modules on the main processor of the smart card, or they can be executed in specialized hardware. An example of such specialized hardware currently used as a cryptographic accelerator to a personal computer is the Luna VPN cryptographic accelerator manufactured by Chrysalis-ITS, Ontario, Canada.

The entire smart card can be protected by a tamper proof package 109, such as the one described in U.S. Pat. No. 5,159,629. The smart card should be tamper evident in the sense that any attempt in determining and/or changing the data in the smart card would result in erasure of this data and/or destruction of some element of the smart card. To prevent tampering with the smart card itself, the packaging can include a trip wire or magnetic circuit forming a closed connection with the sensor and any tampering with the product involves opening the packaging in such a way as to break this connection and trigger an (irreversible) change within the smart card. In certain circumstances the tamper proof feature and encryption may not be necessary.

Other mechanisms can also be used to the same ends of preventing modifications and/or duplication of the smart card or its data content, examples being obtained as easy modification of the invention in U.S. Pat. No. 5,159,629.

The sensor can also be an on-chip pressure sensor or a pressure sensor such as the NPP, NPC or NPH series pressure sensor manufactured by Lucas NovaSensor of Fremont, Calif., with the product packaged under low pressure. Tampering with the product necessitates opening the packaging and allowing outside air to reach this sensor. This change in pressure is recorded by the smart card. For improved protection, the package can also contain a pump to randomly vary the pressure inside the package. In this case the pressure sensor measures the pressure, $P_{sensor}$, inside thee package and compares the sensor reading to the processor command, $P_{computer}$, to the pump. A difference signal can be computed as $$P_{difference}=|P_{Computer}-P_{sensor}|$$

If the $P_{difference}$ is greater than a threshold $P_{thresh}$, then the package is considered to be tampered with.

In yet another implementation, the smart card has a light sensor such as the photodetector MTD3010PM made by Marktech Optoelectronics, Latham, N.Y. The smart card is then packaged so as not to be exposed to light. When the product is tampered with, light will reach this sensor and the smart card will record this change. One may use an optoelectronic sensor which can detect electromagnetic radiation beyond the visual spectrum such as infrared or ultraviolet radiation. Whichever part of the spectrum is used, supplementary sources of radiation can be used, with random levels, as described previously in the case of the pressure sensor, to enhance the security.

Similarly, a temperature sensor such as the TMP03 series sensors manufactured by Analog Devices, Norwood, Mass., can tie used to detect changes in temperature, in applications where the temperature at which a product is shipped has to be maintained in a certain range.

In applications such as in motor vehicles where the detection of shock is needed, an accelerometer such as the Analog Devices ADXL05 or Lucas NovaSensor NAC series accelerometer can be used as the sensor (or as one of the sensors).

In one application of a smart tag vehicle sensor, the smart card records the output of the ADXL05, generates a time stamp and encrypts and stores the result into the memory 103 of the smart tag. In addition, other sensors, such as the TMP03 temperature sensor may also be logged and stored. The vehicle speedometer readings and odometer readings may be time stamped, encrypted also stored in the memory 103. The location of the vehicle is often important in indentifying the types of weather conditions the vehicle has been subjected to, and adding a GPS system whose output is securely recorded in memory may also be added. The combination of the time history of the shock, temperature, speed history, mileage history and geographic location can be used to create a secure vehicle history which can be made available to evaluate the condition of the vehicle.

An example of such a history is summarized below:

| Vehicle History = | | |
|---|---|---|
| | mileage | 50,000 miles |
| | max shock | 10 g |
| | max temperature | 90 F. |
| | minimum temperature | 50 F. |
| | max speed | 85 mph |
| | vehicle location | Florida 90% of miles |
| | | other 10% of miles |

Depending on the product, the sensor (or the combination of sensors) detects mechanical, electromagnetic and thermal properties, and more generally a physical and/or chemical property or a combination thereof. References for sensors detecting chemical properties are found in *An Introduction to Electronic Nose Technology*, by J. Gardner, Neotronics Scientific, Warwick, 1996. Once a change is detected beyond some fixed threshold (or when the data captured by the sensors differs enough from a computed random sequence) at 105, it will be irreversibly recorded within the smart card 101. Time stamping of the event provides a recorded history for the device; secure time stamping can be achieved for instance by attaching a clock or timing unit to the smart card inside the tamper proof package 109.

As shown in FIG. 2, for instance, using such physical properties as piezoelectricity, the sensor 105 such as a Murata PDGS-00LA-TC accelerometer produces a voltage 113 in response to an external force input which results in an acceleration of the sensor. When the electronic signal 113 exceeds some predetermined threshold 110 a comparator 111 is triggered to produce a logic level output to power up the smart card. As a consequence, once a shock is detected greater than a predetermined threshold, it will be irreversibly recorded as a change within the smart card 101. This same concept could be adapted to accommodate random input as an additional means to protect against entering a package containing a product.

The recorded data is encrypted and provides a history of physical events of the product. Anybody in possession of a (possibly public) key can retrieve the data which, once processed by proper algorithms, allows determination of the product state, and allows recognition that the smart card is attached to the product to which it is supposed to be attached. Such analysis can include, but is not limited to, the temperature to which the product was subjected, shocks the product experienced, the first time the product was powered on, etc.

In some cases, if needed, the smart card will also keep a record of the history of changes by also recording the time. In all cases, the change in the product or its environment causes the state of the smart card to be changed irreversibly. This can be effected by the smart card erasing or writing some information in its internal memory.

Any person wishing to determine whether the product is new or not first authenticates the smart card using a zero knowledge protocol. He or she then queries the smart card for the information on whether the product has been opened or been tampered with. If both the authentication is successful and the smart card did not record any change in state, then it can be concluded that the product has not been tampered with.

The smart card can be contactless (by which we mean that no physical contact with the card is needed when performing the authentication or querying) and is embedded into the product or its container: In this case, the authentication and query is made via some remote means. Such technology is currently available. For instance, in RFIDs as disclosed in U.S. Pat. No. 5,682,143 to Michael J. Brady, Thomas Cofino, Harley K. Heinrich, Glen W. Johnson, Paul A. Moskovitz, and George F. Walken. For early references, see, for example, U.S. Pat. No. 4,063,229 to John Welsh and Richard N. Vaughan, U.S. Pat. No. 4,242,663 to Leo Slobodin, and U.S. Pat. No. 4,646,090 to Daniel D. Mawhinney.

For certain products, the output of the sensor 105 is sent to processor 104 which executes a mathematical algorithm to determine a function of the history of the object and/or its environment. For example, milk containers temperature and time history can be used to determine the probability that the milk is sour according to a model, such as shown below:

$$P_{(sour)} = \int_{t_{manufacturedate}}^{t_{currentdate}} f(t, T(t))dt$$

where T is the temperature of the milk container, t is time, and f is a function which can be determined experimentally. The process can result in a message which may or may not be encrypted. For instance, the message may be a visible indicator to the consumer.

Some products (such as wine, food, chemical compounds, or pharmacological products) can deteriorate with no known cause, in which case one cannot use only the control of the environment, but some sensor has to detect intrinsic chemical and/or physical properties of the product. The inventive device could be used to record temperature, humidity, pressure, light, vibration, shock, electromagnetic field, chemical composition, and the opening of the packaging which contain the products.

If the passing of the expiration date is to be detected, the smart card is equipped with a clock or timer which would record the expiration of the product when it occurs.

In another embodiment, the inventive device may be used for detecting and recording changes in consumer electronic products. In addition, to the changes described previously, hours of in-use time (power-on hours) for product may be recorded.

The smart card may be created in an inactive state. After the smart card is attached to the product, the smart card is activated by sending a command to the smart card. This can be done remotely in the case of contactless smart cards. Once activated, the smart card will start monitoring the product and/or its environment. For added security, once activated the smart card cannot be deactivated unless it is destroyed. Alternatively, deactivation would cause an irreversible change in the smart card indicating that the smart card was deactivated after activation.

In yet another preferred embodiment, the smart card could be powered externally, for example by an RF (radiofrequency) energy source. The smart card has micromachined features on chip which are changed (for example, pieces could be broken off) when the product is tampered with. When the user needs to determine whether the product is tampered with, an external power source is applied to power on the smart card. The authentication phase is as before. Next, the micromachined features are sensed either by the smart card or by the user to determined whether tampering has occurred.

While the invention has been described in terms of a preferred embodiment with multiple applications and modifications, those skilled in the art will recognize that the invention can be practiced with modification within the spirit and scope of the appended claims.

We claim:

1. A method of securely recording and storing information in an integrated monitor attached to an object about at least one of physical, chemical and environmental effects on said object, over time, comprising the steps of:

sensing data regarding a change or lack of change of state of said object or an environment of said object, with at least one of a plurality of sensors, said change or lack-of change of state indicating tampering or lack of tampering with said object and/or change or lack of change in said environment of said object;

securely sending a signal of said sensed data from said sensor to a storage device embedded within the monitor; and irreversibly recording using encryption of said signal in said storage device for later retrieval.

2. A method as in claim 1 further comprising the step of recording a time in said storage device for each said signal recorded in said storage device.

3. A method as in claim 1 wherein said sensors detect changes in one or more states of the object selected from the group comprising temperature, humidity, pressure, light, vibration, shock, electromagnetic field, and chemical composition.

4. The method of claim 1, wherein said object is a motor vehicle and said sensors detects at least one of the group comprising: time, mileage, shock, temperature, geographic location, speed, and irreversibly records using encryption said signals in said storage device, creating a time sequence history, of said motor vehicle.

5. The method of claim 1, wherein said object is a packaging container which encloses pharmacological products, food products, or chemical products, and said sensors detect at least one of the group of temperature, humidity, pressure, light, vibration, shock, electromagnetic field, chemical composition, and opening of said packaging container.

6. The method of claim 1, wherein said object is an electronic consumer product and said sensors detect a number of power on hours of said consumer product.

7. A method of recording and storing information in an integrated monitor attached to an object about at least one of physical, chemical and environmental effects on said object over time comprising the steps of:

sensing data regarding a change or lack of change of state of said object, with at least one of a plurality of sensors, said change or lack of change of state indicating tampering or lack of tampering with said object and/or change or lack of change in said environment of said object, processing said data to compute at least one of a plurality of functions of said data;

encrypting at least one of said data and said values of said functions; and irreversibly storing a combination of said encrypted data and values of said functions in a storage device.

8. A method of recording and storing information in an integrated monitor as in claim 7 further comprising displaying on the attached monitor a result from said processing step.

9. A system for securely monitoring the history of a good comprising:
 a storage device on a monitor attached to said good;
 a sensor securely sending a signal of a sensed change or lack of change of a state of said good or an environment of said good to said storage device, said change or lack of change of state indicating tampering or lack of tampering with said good and/or change or lack of change of said environment of said good, and
 an encryption module altering data from said signal being irreversibly recorded in said storage device, for later retrieval.

10. The monitoring system of claim 9 further comprising a processing unit in said attached monitor which acts upon said signals from said sensor.

11. The monitoring system of claim 10 wherein said processing unit acts upon said signal to determine if said signal meets a threshold for recording in said storage device.

12. The monitoring system of claim 10 wherein said processing unit acts upon said signal to execute an algorithm to process said signal to determine a state of said good.

13. The monitoring system of claim 10 further comprising a display in the attached monitor displaying a result determined by said processing unit.

14. The monitoring system of claim 13 wherein said display includes a secure access.

15. The monitoring system as in claim 9, wherein said attached monitor is integrated onto a single silicon substrate.

16. The monitoring system as in claim 9, further comprising a timing unit which sends a time stamp to said storage device to be recorded for each signal recorded from said sensor.

17. The monitoring system as in claim 9, wherein said sensor is comprised of a pressure sensor sending signals to said storage device in response to changes in pressure around said sensor.

18. The monitoring system as in claim 9, wherein said sensor is comprised of a light sensor sending a signal to said storage device when light exposure to said sensor is changed.

19. The monitoring system as in claim 9, wherein said sensor is composed of an electrical correction which if broken sends a signal to said storage device.

20. The monitoring system as in claim 9, further comprising an identification code encrypted in said storage device specific to said good protected by said security system.

21. A monitoring system as in claim 20 wherein said identification code is authenticated using a zero-knowledge protocol.

22. A monitoring system for recording and storing information in an integrated monitor attached to an object about at least one of physical, chemical and environmental effects on said object over time, said system comprising:
 a sensor for sensing data regarding a change or lack of change of state of said object or an environment of said object, said change or lack of change of state indicating tampering or lack of tampering with said object and/or change or lack of change in said environment of said object;
 a processor for computing one of a plurality of functions of said data, a storage device for storing said data and values of said functions of said data in a storage device, and
 an encryption module altering said data so as to be irreversibly stored in said storage device, for later retrieval.

23. A method as in claim 1 wherein said at least one sensor detects said tampering with said object.

* * * * *